United States Patent [19]

Nédelec et al.

[11] 4,335,135
[45] Jun. 15, 1982

[54] 5 AMINO-3,4,5,6 TETRAHYDRO-1H-[-6-]CYCLOHEPT[c,d]INDOLOLS AND A METHOD FOR THEIR USE AS HYPOTENSIVES

[75] Inventors: Lucien Nédelec, Le Raincy; Daniel Fréchet, Paris; Claude Dumont, Nogent sur Marne; Guy Plassard, Savigny sur Orge; Neil L. Brown, Paris, all of France

[73] Assignee: Roussel Uclaf, Paris, France

[21] Appl. No.: 236,610

[22] Filed: Feb. 23, 1981

[30] Foreign Application Priority Data

Feb. 26, 1980 [FR] France ................................ 80 04198
Nov. 18, 1980 [FR] France ................................ 80 24406

[51] Int. Cl.³ ..................... A61K 31/40; C07D 209/80
[52] U.S. Cl. ..................................... 424/274; 548/436
[58] Field of Search ................. 260/326.5 B; 424/274

[56] References Cited

U.S. PATENT DOCUMENTS 3,106,559 10/1963 Sunagawa et al. ............. 260/326.27
3,397,202 8/1968 Plostnieks ....................... 260/326.27

FOREIGN PATENT DOCUMENTS 745495 2/1956 United Kingdom ......... 260/326.5 B

OTHER PUBLICATIONS

Uhle J. ACS, 71, pp. 761-766 (1949).

*Primary Examiner*—David B. Springer
*Attorney, Agent, or Firm*—Hammond & Littell, Weissenberger and Muserlian

[57] ABSTRACT

Novel trans cyclohept[c,d]indolols of the formula

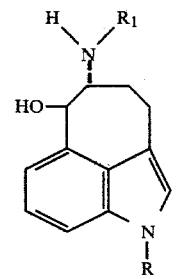

wherein R is selected from the group consisting of hydrogen, alkyl of 1 to 5 carbon atoms and optionally substituted aralkyl of 7 to 12 carbon atoms and $R_1$ is selected from the group consisting of hydrogen, alkyl of 1 to 5 carbon atoms, cycloalkylalkyl of 4 to 7 carbon atoms and optionally substituted aralkyl of 7 to 12 carbon atoms and their non-toxic, pharmaceutically acceptable acid addition salts having hypotensive and antihypertensive activity and a process for their preparation.

12 Claims, No Drawings

5 AMINO-3,4,5,6 TETRAHYDRO-1H-[-6-]CYCLOHEPT[c,d]INDOLOLS AND A METHOD FOR THEIR USE AS HYPOTENSIVES

OBJECTS OF THE INVENTION

It is an object of the invention to provide the novel cyclohept[c,d]indolols of formula I and their non-toxic, pharmaceutically acceptable acid addition salts and a process for their preparation.

It is another object of the invention to provide novel hypotensive and antihypertensive compositions and to provide a novel method of treating arterial hypertension in warm-blooded animals.

These and other objects and advantages of the invention will become obvious from the following detailed description.

THE INVENTION

The novel products of the invention are selected from the group consisting of trans cyclohept[c,d]indolols of the formula

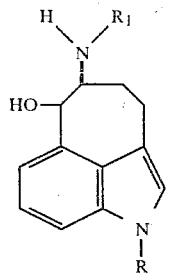

wherein R is selected from the group consisting of hydrogen, alkyl of 1 to 5 carbon atoms and optionally substituted aralkyl of 7 to 12 carbon atoms and $R_1$ is selected from the group consisting of hydrogen, alkyl of 1 to 5 carbon atoms, cycloalkylalkyl of 4 to 7 carbon atoms and optionally substituted aralkyl of 7 to 12 carbon atoms and their non-toxic, pharmaceutically acceptable acid addition salts. The dotted line indicate the OH and —$NHR_1$ are in the trans position.

Examples of suitable alkyl group of 1 to 5 carbon atoms for the compounds of formula I include methyl, ethyl, propyl, isopropyl, butyl, isobutyl and pentyl and aralkyl of 7 to 12 carbon atoms include benzyl and phenethyl optionally substituted with at least one member of the group consisting of bromine, chlorine, methyl, ethyl, methoxy, trifluoromethyl and methylthio. Examples of cycloalkylalkyl of 4 to 7 carbon atoms are cyclopropylmethyl.

Examples of suitable acids for the non-toxic, pharmaceutically acceptable acid addition salts are mineral acids such as hydrochloric acid, hydrobromic acid, hydroiodic acid, nitric acid, sulfuric acid and phosphoric acid and organic acids such as acetic acid, formic acid, propionic acid, benzoic acid, maleic acid, furmaric acid, succinic acid, tartaric acid, citric acid, oxalic acid, glyoxylic acid, aspartic acid, alkanesulfonic acids such as methane sulfonic acid and aryl sulfonic acids such as benzene sulfonic acid.

Preferred compounds of the invention of formula I are those wherein R and $R_1$ are hydrogen or alkyl of 1 to 5 carbon atoms and their non-toxic, pharmaceutically acceptable acid addition salts. Especially preferred are 5-R,S-trans amino-3,4,5,6-tetrahydro-1H-cyclohept[c,-d]indol-6-ol and 5-R,S-trans 5-methylamino-3,4,5,6-tetrahydro-1H-cyclohept[c,d]indol-6-ol and their non-toxic, pharmaceutically acceptable acid addition salts.

The novel processes of the invention for the preparation of the compounds of formula I comprises reacting a compound of the formula

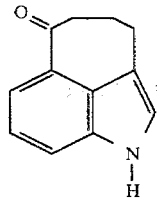

with a halide of the formula R'-Hal III wherein Hal is selected from the group consisting of chlorine, bromine and iodine and R' is R other than hydrogen to obtain a compound of the formula

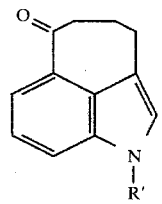

and reacting a compound of formula II or IV with tert.-butyl nitrite in the presence of hydrochloric acid to obtain a compound of the formula

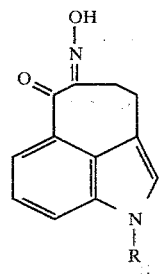

and reducing the latter to obtain a compound of the formula

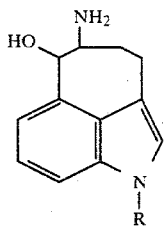

which is a compound of formula I wherein $R_1$ is hydrogen and, if desired, salifying the compound of formula $I_A$ or reacting the compound of formula $I_A$ with trifluoroacetic acid anhydride, preferably in the presence of a base to obtain a compound of the formula

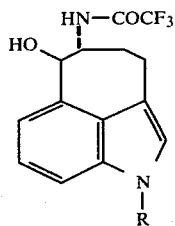

VI reacting the latter with a halide of the formula R₁'-Hal wherein Hal has the above definition and R₁' is R₁ except for hydrogen to obtain a compound of the formula

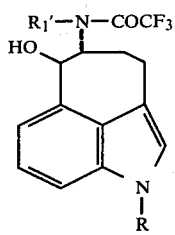

VIII wherein R and R₁' has the above definition and reacting the latter with an agent capable of hydrolyzing the trifluoroacetamide group to form a compound of the formula

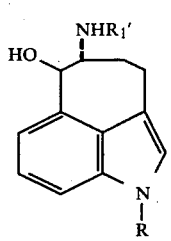

I$_B$ which is a compound of formula I wherein R₁ is other than hydrogen which, if desired, may be salified or reacting a compound of formula I$_A$ with an alkyl haloformate to obtain a compound of the formula

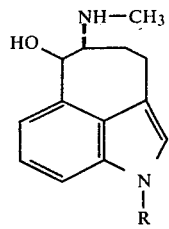

I$_C$ which is a compound of formula I wherein R₁ is methyl which, if desired, may be salified or reacting a compound of formula I$_A$ with an acetylation agent to obtain a compound of the formula

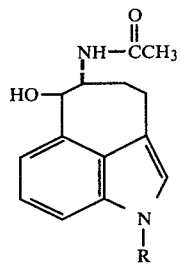

X and reducing the latter to obtain a compound of the formula

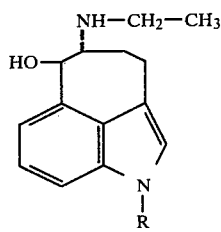

I$_D$ which is a compound of formula I wherein R₁ is ethyl which, if desired, may be salified or reacting a compound of formula I$_A$ with acetone in a reducing medium to obtain a compound of the formula

IX wherein Alk is alkyl of 1 to 4 carbon atoms and reducing the latter to form a compound of the formula

I$_E$ which is a compound of formula I wherein R₁ is isopropyl which, if desired, may be salified.

In a preferred mode of the process of the invention, the reaction of the compounds of formulae II and III is effected by the transfer of phase by the technique of Bosco et al. [Synthesis, Vol. 2 (1976), p. 124] for example, in the presence of tetrabutyl ammonium chloride, benzyltriphenylphosphonium chloride or preferably tetrabutyl ammonium acid sulfate, aqueous sodium hydroxide and benzene. The reduction of the compounds of formula V is effected by catalytic hydrogenation followed by sodium borohydride treatment. The reaction of the compound of formula $I_4$ with trifluoroacetic acid anhydride is effected in the presence of an inorganic base. The reaction of the compounds of formulae VI and VII is effected in the presence of a basic agent such as an alkali metal hydroxide or alkali metal carbonate or tertiary amine.

The hydrolysis of the compound of formula VIII is preferably effected with sodium hydroxide or potassium hydroxide and the reaction of a compound of formula $I_4$ and an alkyl haloformate is effected in the presence of a base such as an alkali metal carbonate. The reduction of the compounds of formulae IX and X is effected with lithium aluminum hydride and the acetylation of the compounds of formula $I_4$ is acetyl chloride, acetyl bromide or acetic acid anhydride. The reducing agent for the reaction of acetone and the compounds of formula $I_4$ may be sodium cyanoborohydride. The salification is effected by reacting stoichiometric amounts of an acid and the compounds of formula I.

The novel hypotensive and antihypertensive compositions of the invention are comprised of an hypotensively and antihypertensively effective amount of at least one compound of formula I and their non-toxic, pharmaceutically acceptable acid addition salts and an inert pharmaceutical carrier. The compositions may be in the form of tablets, dragees, gelules, capsules, granules, suppositories and injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

Among the preferred compositions of the invention are those containing compounds of formula I wherein R and $R_1$ are hydrogen or alkyl of 1 to 5 carbon atoms and their non-toxic, pharmaceutically acceptable acid addition salts. Specific compositions are those wherein the compounds are selected from the group consisting of 5-R,S-trans amino-3,4,5,6-tetrahydro-1H-cyclohept[c,d]indol-6-ol and 5-R,S-trans 5-methylamino-3,4,5,6-tetrahydro-1H-cyclohept[c,d]indol-6-ol and their non-toxic, pharmaceutically acceptable acid addition salts.

The compositions of the invention are useful for the treatment of essentially arterial hypertension, hypertension of fifties; of menopause, of diabetic, of obesity and of plethoric as well as for the treatment of hypertension due to aging, of atherosclerosis and in the treatment of hypertension of renal origin.

The novel method of the invention for inducing hypotensive and antihypertensive activity in warm-blooded animals, including humans, comprises administering to warm-blooded animals an hypotensively and antihypertensively effective amount of at least one compound of formula I and their non-toxic, pharmaceutically acceptable acid addition salts. The compounds may be administered orally, rectally or parentally and the usual daily dose depending upon the method of administration and the compound being administered, can be, for example, from 0.1 to 4 mg/kg per day with the compound of example I by oral route in the adult.

In the following examples there are described several preferred embodiments to illustrate the invention. However, it should be understood that the invention is not intended to be limited to the specific embodiments.

EXAMPLE 1

5-R,S-trans amino-3,4,5,6-tetrahydro-1H-cyclohept[c,d]indol-6-ol and its acetate

STEP A: 5-oxime of 3,4-dihydro-1H-cyclohept[c,d]indol-5,6-dione 22 ml of 5 N hydrochloric acid in ethanol were added under nitrogen to a stirred solution of 18.5 g of 3,4-dihydro-1H-cyclohept[c,d]indol-6-one [Chem. Pharm. Bull., Vol. 25 (11) (1977), pg. 3023] in 185 ml of tetrahydrofuran cooled in an ice bath and then 13.5 ml of tert.-butyl nitrite were added thereto. The mixture was stirred in the ice bath for 30 minutes and was then vacuum filtered and the recovered product was washed with ether and dried under reduced pressure at 80° C. to obtain 19.4 g of 5-oxime of 3,4-dihydro-1H-cyclohept[c,d]indol-5,6-dione melting at 235° C. with decomposition.

STEP B: 5-R,S-trans amino-3,4,5,6-tetrahydro-1H-cyclohept [c,d]indol-6-ol and its acetate 2.5 g of 10% palladized activated carbon were added to a suspension of 5 g of the product of Step A in 100 ml of methanol and the mixture was stirred under hydrogen at room temperature for 40 minutes and was then vacuum filtered. The filtrate was cooled in an ice bath and 2.5 g of sodium borohydride were added thereto over 10 minutes and the mixture was stirred at room temperature under an inert atmosphere for 1 hour. The mixture was evaporated to dryness and the residue was taken up in refluxing methylene chloride. The mixture was filtered and the filtrate was evaporated to dryness. The residue was dissolved in 7 ml of methanol at 50° C. and 70 ml of ethyl acetate were added to the mixture which was then filtered. The filter was rinsed with ethyl acetate and the filtrate was concentrated to 50 ml and 25 ml of 1.1 N acetic acid in ethyl acetate were added thereto. The mixture stood at room temperature for one hour, was iced for 30 minutes and vacuum filtered and the product was dried under reduced pressure at 70° C. to obtain 4.9 g of the acetate of 5-R,S trans amino-3,4,5,6-tetrahydro-1H-cyclohept[c,d]-indol-6-ol melting at 150° C. After crystallization from a 1-1 methanol-ethyl acetate mixture, the acetate occured in the form of white crystals melting at 165° C.

Analysis: $C_{12}H_{14}N_2O.C_2H_4O$: molecular weight=262.30; Calculated: %C: 64.10; %H: 6.92; %N: 10.68; Found: 64.2; 7.1; 10.4.

10.8 g of the said acetate were suspended in 300 ml of ethyl acetate and 100 ml of concentrated ammonium hydroxide were added thereto with stirring. The mixture was saturated with sodium chloride and the mixture was stirred under nitrogen for 15 minutes. The decanted organic phase was washed with aqueous sodium chloride, was dried and evaporated to dryness to obtain 9.8 g of 5-R,S-trans amino-3,4,5,6-tetrahydro-1H-cyclohept[c,d]-indol-6-ol.

EXAMPLE 2

R,S-trans
5-methylamino-3,4,5,6-tetrahydro-1H-cyclohept[c,d]indol-6-ol hydrochloride

STEP A: Ethyl R,S-trans-N-(6-hydroxy-3,4,5,6-tetrahydro-1H-cyclohept[c,d] indol-5-yl)-carbamate 2.6 ml of ethyl chloroformate were added with stirring at room temperature over 10 minutes to a mixture of 2.62 g of the acetate of Example 1, 40 ml of water, 52 ml of ethyl acetate and 2.62 g of potassium carbonate and the mixture was stirred for one hour and was evaporated to dryness under reduced pressure. The residue was diluted with a little ice water and the mixture was triturated at room temperature for 30 minutes and was vacuum filtered. The product was dried under reduced pressure at 60°–70° C. and was then added to methanol with stirring. The mixture was filtered and the filtrate was concentrated. Crystallization was induced and the mixture was iced for 3 hours and was filtered to obtain 1.45 g of ethyl R,S-trans-N-(6-hydroxy-3,4,5,6-tetrahydro-1H-cyclohept[c,d] indol-5-yl)-carbamate in the form of crystals melting at 190° C.

STEP B: R,S-trans 5-methylamino-3,4,5,6-tetrahydro-1H-cyclohept[c,d] indol-6-ol hydrochloride A solution of 1.83 g of the product of Step A in 75 ml of dioxane were added over 20 minutes with stirring under an inert atmosphere at room temperature to a suspension of 3.6 g of aluminum-lithium hydride in 50 ml of tetrahydrofuran and the mixture was refluxed for 2 hours and was cooled. 50 ml of tetrahydrofuran containing 10% water were added over 30 minutes to the mixture which was then diluted with 50 ml of water and filtered. The filter was rinsed with ethyl acetate and sodium chloride was added to the filtrate. The decanted aqueous phase was extracted with ethyl acetate and the organic phase was washed with water, with aqueous saturated sodium chloride solution, dried over sodium sulfate and evaporated to dryness to obtain 2 g of raw R,S-trans 5-methylamino-3,4,5,6-tetrahydro-1H-cyclohept[c,d] indol-6-ol. The said product was dissolved in 3 ml of ethanol and 1.5 ml of 5 N hydrochloric acid in ethanol were added thereto dropwise. The mixture was iced for one hour and was filtered. The product was washed with ethanol and dried under reduced pressure at 70° C. to obtain 1.24 g of R,S-trans 5-methylamine-3,4,5,6-tetrahydro-1H-cyclohept[c,d] indol-6-ol hydrochloride melting at 224° C. with decomposition.

Analysis: $C_{13}H_{16}N_2O \cdot HCl$; molecular weight=252.7; Calculated: %C: 61.78; %H: 6.78; %N: 11.08; %Cl: 14.03; Found: 61.8; 6.7; 11.1; 13.9.

EXAMPLE 3

R,S, trans
5-isopropylamino-3,4,5,6-tetrahydro-1H-cyclohept[c,d] indol-6-ol 10.5 g of sodium cyanoborohydride were added over 15 minutes with stirring under an inert atmosphere to a suspension of 10.5 g of the product of Example 1 in 105 ml of methanol and 52.2 ml of acetone cooled to 0° C. were added and the mixture was stirred at 0° C. for 3½ hours and was filtered. The filter was rinsed with ethyl acetate and the filtrate was evaporated to dryness. The residue was chromatographed over silica gel and was eluted with a 7-2-1 benzene-ethyl acetatetriethylamine mixture to obtain 6.32 g of crystals which were dissolved in 6 ml of hot ethyl acetate. The mixture was cooled for 90 minutes and was then vacuum filtered. The product was dried at room temperature under reduced pressure to obtain 4.03 g of R,S-trans 5-isopropylamino-3,4,5,6-tetrahydro-1H-cyclohept[c,d] indol-6-ol in the form of white crystals melting at 100° C.

Analysis: $C_{15}H_{20}N_2O$; molecular weight=244.338; Calculated: %C: 73.74; %H: 8.25; %N: 11.46; Found: 73.5; 8.3; 11.4.

EXAMPLE 4

5-R,S-trans
5-amino-1-methyl-3,4,5,6-tetrahydro-1H-cyclohept [c,d] indol-6-ol acetate

STEP A: 1-methyl-1,3,4,5-tetrahydro-6H-cyclohept[c,d] indol-6-one

A mixture of 5 g of 3,4-dihydro-1H-cyclohept[c,d] indol-6-one, 50 ml of benzene, 2.5 ml of methyl iodide, 25 ml of 5 N sodium hydroxide solution and 9.2 g of tetra-n-butyl ammonium acid sulfate was stirred for 30 minutes under an inert atmosphere at 40°–45° C. and the mixture was diluted with water. The decanted aqueous phase was extracted with ethyl acetate and the organic phase was washed with N hydrochloride acid, with water, dried and evaporated to dryness. The residue was chromatographed over silica gel and was eluted with a 95-5 chloroform-ethyl acetate mixture to obtain 6.5 g of raw product. The latter was crystallized from isopropanol to obtain 5.15 g of 1-methyl-1,3,4,5-tetrahydro-6H-cyclohept [c,d,] indol-6-one melting at ≃70° C.

STEP B: 5-oxime of 1-methyl-3,4-dihydro-1H-cyclohept[c,d] indol-5,6-dione 85 ml of ether were added at −5° C. under an inert atmosphere to a solution of 10.41 g of the product of Step A in 20 ml of tetrahydrofuran and then 16.4 ml of 3.5 N hydrochloric acid in ethanol were added thereto. The mixture was stirred for 5 minutes and then 7 ml of tert.-butyl nitrite were added thereto over 30 minutes. The mixture was stirred at 0° C. for 30 minutes and was vacuum filtered. The product was washed with ether and dried over reduced pressure to obtain 10.5 g of 5-oxime of 1-methyl-3,4-dihydro-1H-cyclohept[c,d] indol-5,6-dione metling at 190° C., then 200° C.

STEP C: 5-R,S-trans 5-amino-1-methyl-3,4,5,6-tetrahydro-1H-cyclohept[c,d] indol-6-ol acetate A mixture of 10.5 g of the product of Step B, 5.25 g of 10% palladized carbon and 210 ml of methanol was stirred under hydrogen for 105 minutes and was then filtered. The filtrate was cooled in a ice bath and 5.25 g of sodium borohydride were added thereto over 10 minutes under an inert atmosphere. The mixture was stirred in the bath for 10 minutes and for 40 minutes at room temperature. The methanol was distilled under reduced pressure and 30 ml of water wre added thereto. The mixture was extracted with ethyl acetate and the organic phase was washed with water, dried and evaporated to dryness under reduced pressure. The residue was chromatographed over silica gel and was eluted with a 90-5-5 ethyl acetate-methanol-ammonium hydroxide mixture to obtain 9.1 g of 5-R,S,-trans 5-amino-1-methyl-3,4,5,6-tetrahydro-1H-cyclohept[c,d] indol-6-ol. The said product was dissolved in 10 ml of ethanol and an excess of a solution of acetic acid in ethyl acetate was slowly add-d thereto. The mixture stood for 48 hours and was then vacuum filtered. The product was washed with ethanol, ethyl acetate and then ether and was dried to obtain 4.12 g of 5-R,S-trans 5-amino-1-methyl-3,4,5,6-tetrahydro-1H-cyclohept [c,d] indol-6-ol acetate melting at ≃140° C. and then 160° C. after crystallization in isopropanol.

Analysis: $C_{15}H_{20}N_2O_3$; molecular weight=276.336; Calculated: %C: 65.19; %H: 7.29; %N: 10.13; Found: 65.2; 7.4; 10.2.

EXAMPLE 5

Tablets were prepared containing 10 mg of the acetate of 5-R,S-trans amino-3,4,5,6-tetrayhydro-1H-cyclohept [c,d] indol-6-ol or 15 mg of trans 5-methylamino-3,4,5,6-tetrahydro-1H-cyclohept[c,d] indol-6-ol hydrochloride and sufficient excipient of lactose, starch, talc and magnesium stearate for a final weight of 100 mg.

PHARMACEUTICAL STUDY

A. Antihypertensive Activity

The antihypertensive activity of the compound of Example 1 was determined on Beagle dogs weighing between 12 and 14 kg made hypertensive by wrapping the 2 kidneys with cellophane by the technique of Irvine H. Page [Science, Vol. 89 (1939), p. 273–274]. The test product was administered orally at doses of 1 and 10 mg/kg and the arterial pressure was measured on the tail by a pneumatic collar and with the aid of a piezoelectric pressure transducer. The pressure was measured before and 1,3,6-and 24 hours after the product administration and the percentage of arterial pressure variation after administration of the product was compared to the initial control pressure. The results are reported in Table I.

TABLE I

| Product of Example | Dose in mg/kg | % arterial pressure variation after | | | |
|---|---|---|---|---|---|
| | | 1 hr. | 3 hr. | 6 hr. | 24 hr. |
| 1 | 1 | −16 | −17 | −13 | −10 |
| | 10 | −11 | −27 | −10 | −32 |

B. Antihypertensive Activity

The antihypertensive activity was studied on spontaneously hypertensive male rats of Okamato strain 20 weeks old weighing between 300 and 320 g. The test product was orally administered 48 hours after the placing of an intracarotidin catheter and the arterial pressure was measured on the rat's tail with a pneumatic collar and a piezo-electric pressure transducer. The pressure was determined before and 1,4 and 24 hours after the administration of the test product and the percent of variation was determined as in A. The results are reported in Table II.

TABLE II

| Product of Example | Dose in mg/kg | % arterial pressure variation after | | |
|---|---|---|---|---|
| | | 1 hr. | 4 hr. | 24 hr. |
| 1 | 1 | −24 | −21 | −12 |

C. Hypotensive Activity

The hypotensive activity was studied on male rats of the Wistar strain weighing about 300 g and anesthesized with nembutal (50 mg/kg-intraveinously). The test compound was administered intraveinously through the jugular vein and carotidin arterial pressure was measured before and after the test product administration. The arterial pressure difference were calculated as for Table I and the results are reported in Table III.

TABLE III

| Product of Example | Dose in mg/kg | % arterial pressure variation after minutes | | | |
|---|---|---|---|---|---|
| | | 1 | 5 | 10 | 30 |
| 1 | 0.1 | −3 | −15 | −28 | −34 |
| | 0.01 | 0 | −7 | −16 | −16 |
| 2 | 1 | −11 | −28 | −34 | −30 |
| | 0.1 | −1 | −12 | −17 | −10 |
| 3 | 10 | −34 | −31 | −26 | −29 |
| | 1 | −15 | −18 | −18 | −21 |
| 4 | 10 | −31 | −21 | −15 | 0 |

D. Acute toxicity

The acute toxicity was determined on groups of mice who orally received the test compounds to determine the $DL_O$ dose or the maximum dose at which no mice were killed after 8 days. The results are reported in Table IV.

TABLE IV

| Product Example | $DL_0$ in mg/kg |
|---|---|
| 1 | 200 |
| 2 | 200 |
| 3 | 100 |
| 4 | 200 |

Various modifications of the products and processes of the invention may be made without departing from the spirit or scope thereof and it should be understood that the invention is intended to be limited only as defined in the appended claims.

We claim:

1. A compound selected from the group consisting of trans cyclohept[c,d] indolols of the formula

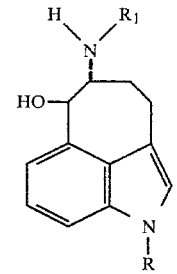

wherein R is selected from the group consisting of hydrogen, alkyl of 1 to 5 carbon atoms and optionally substituted aralkyl of 7 to 12 carbon atoms and $R_1$ is selected from the group consisting of hydrogen, alkyl of 1 to 5 carbon atoms, cycloalkylalkyl of 4 to 7 carbon atoms and optionally substituted aralkyl of 7 to 12 carbon atoms substituted with at least one member selected from the group consisting of bromine, chlorine, methyl, ethyl, methoxy, trifluoromethyl, and methylthio, and their non-toxic, pharmaceutically acceptable acid addition salts.

2. A compound of claim 1 wherein R and $R_1$ are selected from the group consisting of hydrogen and alkyl of 1 to 5 carbon atoms.

3. A compound of claim 1 selected from the group consisting of 5-R,S-trans amino-3,4,5,6-tetrahydro-1H-cyclohept[c,d] indol-6-ol and its non-toxic, pharmaceutically acceptable acid addition salts.

4. A compound of claim 1 selected from the group consisting of 5-R,S-trans 5-methylamino-3,4,5,6-tetrahydro-1H-cyclohept[c,d] indol-6-ol and its non-toxic, pharmaceutically acceptable acid addition salts.

5. A composition for the treatment of hypertension comprising an antihypertensively effective amount of at least one compound of claim 1 and inert pharmaceutical carrier.

6. A composition of claim 5 wherein R and $R_1$ are selected from the group consisting of hydrogen and alkyl of 1 to 5 carbon atoms.

7. A composition of claim 5 wherein the compound is selected from the group consisting of 5-R,S-trans amino-3,4,5,6-tetrahydro-1H-cyclohept[c,d] indol-6-ol and its non-toxic, pharmaceutically acceptable acid addition salts.

8. A composition of claim 5 wherein the compound is selected from the group consisting of 5-R,S-trans 5-methylamino-3,4,5,6-tetrahydro-1H-cyclohept[c,d] indol-6-ol and its non-toxic, pharmaceutically acceptable acid addition salts.

9. A method of inducing hypotensive activity in warm-blooded animals comprising administering to warm-blooded animals an hypotensively effective amount of at least one compound of claim 1.

10. A method of claim 9 wherein R and $R_1$ are selected from the group consisting of hydrogen and alkyl of 1 to 5 carbon atoms.

11. A method of claim 9 the compound is selected from the group consisting of 5-R,S,-trans amino-3,4,5,6-tetrahydro-1H-cyclohept[c,d]indol-6-ol and its non-toxic, pharmaceutically acceptable acid addition salts.

12. A method of claim 9 the compound is selected from the group consisting of 5-R,S-trans 5-methylamino-3,4,5,6-tetrahydro-1H-cyclohept [c,d]indol-6-ol and its non-toxic, pharmaceutically acceptable acid addition salts.

* * * * *